United States Patent [19]

Langer, Jr. et al.

[11]  4,268,455
[45]  May 19, 1981

[54] CHELATING TERTIARY AMINO METAL AMIDES

[75] Inventors: Arthur W. Langer, Jr., Watchung; Thomas A. Whitney, Roselle, both of N.J.

[73] Assignee: Exxon Research & Engineering Co., Florham Park, N.J.

[21] Appl. No.: 713,902

[22] Filed: Aug. 12, 1976

[51] Int. Cl.³ ................................................ C07F 5/06
[52] U.S. Cl. ..................... 260/448 R; 260/448 A; 260/429.7; 260/429.9; 260/429.3; 260/429 J; 564/9; 564/305; 564/367; 564/368; 564/457; 564/461; 564/462; 564/511; 564/512
[58] Field of Search ............ 260/448 R, 583 R, 429.7, 260/563 R, 429.9, 438.1, 563 C, 429.3, 583 P, 448 A, 429 J, 577

[56] References Cited

U.S. PATENT DOCUMENTS

| | | | |
|---|---|---|---|
| 3,555,020 | 1/1971 | Shepherd | 260/563 C X |
| 3,577,414 | 5/1971 | Shepherd | 260/563 C X |
| 3,647,803 | 3/1972 | Schlott et al. | 260/563 C X |
| 3,734,963 | 5/1973 | Langer et al. | 260/563 R |
| 3,751,384 | 8/1973 | Langer | 260/577 X |
| 3,755,533 | 8/1973 | Langer et al. | 260/577 X |
| 3,758,580 | 9/1973 | Langer et al. | 260/429 J X |
| 3,758,585 | 9/1973 | Bunting | 260/583 P |
| 3,769,345 | 10/1973 | Langer | 260/563 R |
| 3,917,602 | 11/1975 | Normant | 260/563 C X |
| 3,933,879 | 1/1976 | Langer et al. | 260/448 R |
| 4,152,401 | 5/1979 | Langer et al. | 260/429 J X |

Primary Examiner—Paul F. Shaver
Attorney, Agent, or Firm—J. J. Allocca; Edward M. Corcoran

[57] ABSTRACT

Chelating tertiary amino metal amides selected from compounds having the formulae: $Mg^{++}$ [Chel N]$_2^{\ominus}$ wherein [Chel N]$^{\ominus}$ is not

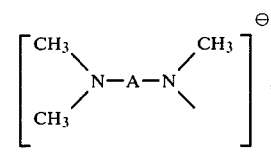

[Chel N]$^{\ominus}$M$^{\oplus}$, [Chel N]$^{\ominus}$M$^{\oplus}$M'H$_m$R$_n$X$_p$, Z Mg$^{\oplus}$[Chel N—M'H$_m$R$_n$X$_p$]$^{\ominus}$, Mg$^{++}$ —[Chel N—M'H$_m$R$_n$X$_p$]$^{\ominus}$[M'H$_m$R$_n$X$_p$Z]$^{\ominus}$, Chel N-Mg$^{\oplus}$[N—Mg$^{\oplus}$H$_m$R$_n$X$_p$Z]$^{\ominus}$ and Mg$^{++}$ [Chel N—M'H$_m$R$_n$X$_p$]$_2^{\ominus}$, wherein M is a Group IA metal, M' is a metal selected from the group consisting of Li, Na, Mg, Be, Zn, Cd, B, Al, Ga, In, Zr, Ti, Sn and Cu and m and n = 0 to 4, p = 0 to 3 and (m+n+p) = the valence of M' and (m+n) = at least 1 and X is a nonreactive group selected from the group consisting of chlorine, bromine, iodine, $C_1$ to $C_{20}$ alkoxide, $C_1$ to $C_{20}$ thioalkoxide, $C_2$ to $C_{40}$ hydrocarbyl secondary amide and $C_2$ to $C_{40}$ hydrocarbyl secondary phosphide, R is hydrocarbyl group and Z is selected from the group consisting of R, X and H.

In an alternative embodiment, the instant invention relates to chiral optically active chelating tertiary amino metal amides selected from compounds having the formulae: [Chel*N]$^{\ominus}$M$^{\oplus}$; [Chel*N]$^{\ominus}$M$^{\oplus}$M'H$_m$R$_n$X$_p$, Z Mg$^{\oplus}$[Chel*N—M'H$_m$R$_n$X$_p$]$^{\ominus}$, Mg$^{++}$ [Chel*-N—M'H$_m$R$_n$X$_p$]$^{\ominus}$[M'H$_m$R$_n$X$_p$Z]$^{\ominus}$, Chel*-N—Mg$^{\oplus}$[M'H$_m$R$_n$X$_p$]$^{\ominus}$, Mg$^{++}$[Chel*-N—M'H$_m$R$_n$X$_p$]$_2^{\ominus}$ and Mg$^{++}$ [Chel*N]$_2^{\ominus}$ wherein M, M', R, X, m, n, p and Z are as defined previously and where * denotes optical activity.

The compounds of the instant invention are useful in metalations, synthesis, asymmetric synthesis and other reactions. When chiral optically active chelating tertiary amino metal amides are used, the reactions which can be performed include all of the above, plus other reactions which produce chiral or stereoregular products.

21 Claims, No Drawings

CHELATING TERTIARY AMINO METAL AMIDES

This invention relates to a new class of chelating tertiary amino metal amide compositions. In one aspect, this invention relates to a class of chiral, optically active chelating tertiary amino metal amides. In another aspect, this invention relates to an asymmetric synthesis process which reacts optically active chelating tertiary amino metal amides with prochiral substrates to yield optically active products.

PRIOR ART

One of the coinventors of the subject application has disclosed and claimed in U.S. Pat. No. 3,451,988 various compositions of matter which include a type of chelated metal amide composition typically having the formula Chel.LiNR$_2$ wherein Chel is a tertiary chelating polyamine.

In the instant invention the new compositions are chelating tertiary amino metal amides. These are derived from polyamines containing at least one secondary amino group. Thus, in the instant invention, the amide function is an integral part of the chelating polyamine.

Coates et al in numerous publication (J. Chem. Soc. (A), 1966, 26); J. Chem. Soc. (A)(11), 1968, 2561); (J. Chem. Soc. (A), 1968, 514); (J. Chem. Soc. (A), 1969, 56); (J. Chem. Soc. (A) 1962, 3340) disclose compounds of the formula:

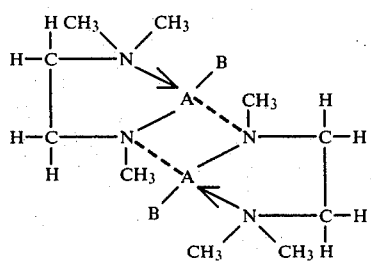

wherein A is selected from the group consisting of Mg, Be and Zn and B is selected from the group consisting of methyl, ethyl, isopropyl and tert. butyl. They reveal that compounds of this formula may exist in either dimer or monomer form depending upon the choice of R group, the larger the R group, the greater the steric hindrance, resulting in formation of monomer.

The compounds discussed by Coates et al are only derivatives of trimethylethylenediamine (Tri-MED) in combination with Mg, Be and Zinc. There is no indication in the articles that tertiary amine materials other than Tri-MED will successfully form complexes with Group IA metals or Mg, nor for that matter that even Tri-MED will successfully chelate with Group IA metal materials. When the chiral, optically active chelating tertiary amino metal amides discussed in the instant invention are considered, the Coates et al references are not relevant since only after a compound or series of compounds which are representative of the class of optically active compounds under consideration have been synthesized can one state with certainty that such optically active compounds can be made. The reason is that such optical active chelating tertiary amino metal amides could undergo self-induced racemization thereby making it impossible to prepare such a series of compounds. When one deals with chiral optically active compositions in synthesis reactions there is no certainty until after the materials have actually been prepared that optically active products will result. Coates et al never synthesized chiral optically active compounds nor did they predict that such compounds could indeed be prepared or that they would have any utility in asymmetric synthesis. Furthermore, nowhere does Coates teach or suggest compounds containing complex anions of the type M+[Chel—N—M'H$_m$R$_n$X$_p$]$^\ominus$ or the corresponding Mg compositions of this invention.

The chelating tertiary amino metal amide compositions of this invention have the formulae: Mg(++) [Chel N]$_2$$^\ominus$ wherein [Chel N]$^\ominus$ is not

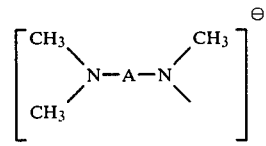

[Chel N]—$^\ominus$ M$^\oplus$, [Chel N]$^\ominus$M$^\oplus$M'H$_m$R$_n$X$_p$, Z Mg$^\oplus$[Chel N-M'H$_m$R$_n$X$_p$]$^\ominus$, Mg(++) [Chel N—M'H$_m$R$_n$X$_p$]$^\ominus$[M'H$_m$R$_n$X$_p$Z]$^\ominus$, Chel N—Mg$^\oplus$-[M'H$_m$R$_n$X$_p$Z]$^\ominus$ and Mg(++) [Chel N—M'H$_m$R$_n$X$_p$]$_2$$^\ominus$, wherein [Chel N]$^\ominus$ has the formula selected from the group consisting of:

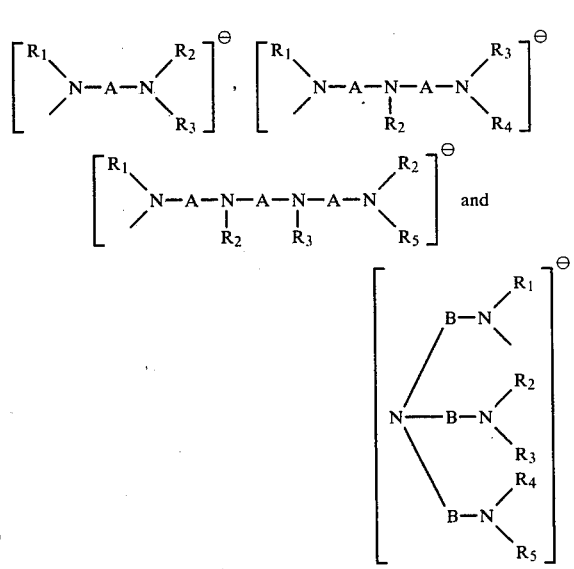

wherein R$_1$ is a C$_1$ to C$_{20}$ hydrocarbyl radical; R$_2$, R$_3$, R$_4$ and R$_5$ are the same or different alkyl or aryl radicals of 1 to 7 carbon atoms inclusive; A is selected from the group consisting of a nonreactive group containing 2 to 3 methylenic radicals having 0 to 6 monovalent substituents containing 1 to 10 carbon atoms or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 0 to 3 monovalent substituents containing 1 to 10 carbon atoms, M is a Group IA metal, M' is a metal selected from the group consisting of lithium, sodium, beryllium, magnesium, zinc, copper, cadmium, boron, aluminum, gallium, indium, zirconium, titanium and tin and m and n=0 to 4, p=0 to 3, (m+n+p)=the valence of M' and (m+n)=at least 1; R is a hydrocarbyl group selected from the group consisting of $C_1$-$C_{30}$ alkyl, $C_6$-$C_{30}$ aryl, $C_7$-$C_{30}$ aralkyl, $C_3$-$C_{30}$ naphthenic, $C_2$-$C_{30}$ alkenyl, $C_2$-$C_{30}$ alkynyl and cyclopentadienyl; X is a nonreactive group selected from the group consisting of chlorine, bromine, iodine, $C_1$-$C_{20}$ alkoxide, $C_1$-$C_{20}$ thioalkoxide, $C_2$-$C_{40}$ hydrocarbyl secondary amide and $C_2$-$C_{40}$ hydrocarbyl secondary phosphide, and Z is selected from the group R, X or H.

Suitable nonlimiting examples of chelating tertiary amino amides, [Chel N]$^\ominus$, of this invention include compounds having the following structures:

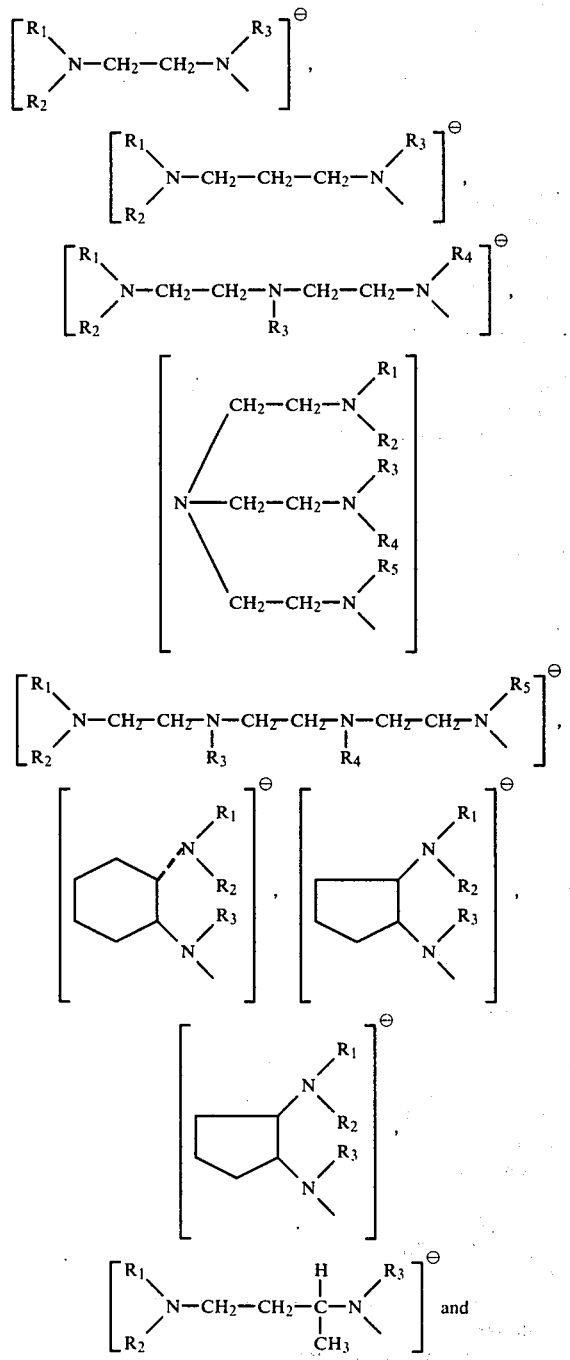

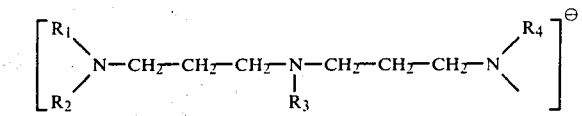

wherein $R_1$ is a $C_1$ to $C_{20}$ hydrocarbyl radical; $R_2$, $R_3$, $R_4$ and $R_5$ are the same or different alkyl or aryl radicals of 1 to 7 carbon atoms inclusive.

Most preferably, the chelating tertiary amino metal amides of this invention are chiral compounds having the formula:

[Chel*N]$^\ominus$M$^\oplus$,
[Chel*N]$^\ominus$M$^\oplus$M'H$_m$R$_n$X$_p$, Z Mg$^\oplus$[Chel*-N—M'H$_m$R$_n$X$_p$]$^\ominus$, Mg$^{++}$ —[Chel*N—M'H$_m$R$_n$X$_p$]$^\ominus$[M'H$_m$R$_n$X$_p$Z]$^\ominus$, Chel*N—Mg$^\oplus$[M'H$_m$R$_n$X$_p$Z]$^\ominus$, Mg$^{++}$ [Chel*N—M'H$_m$R$_n$X$_p$]$_2$$^\ominus$, and Mg$^{++}$ [Chel*N]$_2$$^\ominus$, wherein [Chel*N]$^\ominus$ has a formula selected from the group:

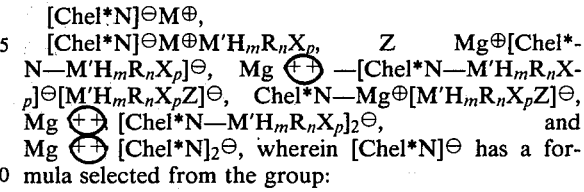

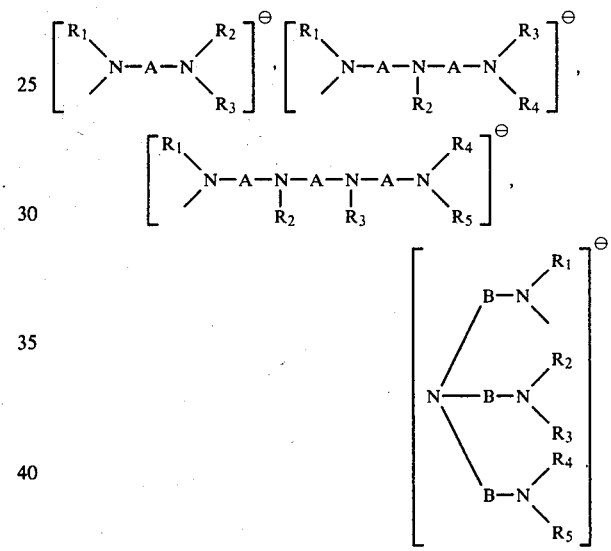

wherein $R_1$ is a $C_1$ to $C_{20}$ hydrocarbyl radical; $R_2$, $R_3$, $R_4$ and $R_5$ are the same or different alkyl or aryl radicals of 1 to 7 carbon atoms inclusive; A is selected from the group consisting of a nonreactive group containing 2 to 3 methylenic radicals having 1 to 6 monovalent substituents containing 1 to 10 carbon atoms, or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 1 to 3 monovalent substituents containing 1 to 10 carbon atoms such that the chelating tertiary amino amide does not have a center, plane or alternating axis of symmetry; M is a Group IA metal; M' is a metal selected from the group consisting of lithium, sodium, beryllium, magnesium, zinc, copper, cadmium, boron, aluminum, gallium, indium, zirconium, titanium, and tin and m and n=0 to 4, p=0 to 3, (m+n+p)=the valence of M' and (m+n)=at least 1; R is a hydrocarbyl group selected from the group consisting of $C_1$-$C_{30}$ alkyl, $C_6$-$C_{30}$ aryl, $C_7$-$C_{30}$ aralkyl, $C_3$-$C_{30}$ naphthenic, $C_2$-$C_{30}$ alkenyl, $C_2$-$C_{30}$ alkynyl and cyclopentadienyl, X is a nonreactive group selected from the group consisting of chlorine, bromine, iodine, $C_1$-$C_{20}$ alkoxide, $C_1$-$C_{20}$ thioalkoxide, $C_2$-$C_{40}$ hydrocarbyl secondary amide and $C_2$-$C_{40}$ hydrocarbyl secondary phosphide, Z is selected from the group R, X or H, and * denotes optical activity. Suitable R, X and Z groups may optionally contain an asymmetric center.

Suitable nonlimiting examples of $M'H_mR_nX_p$ include $LiC_4H_9$, $NaC_6H_5$, $CuC_4H_9$, $Mg(C_6H_5)_2$, $Zn(C_2H_5)_2$, $LiC_6H_4C_{24}H_{49}$, $Be(C_4H_9)_2$, $Cd(CH_3)_2$, $LiCH_2$—$CH$=$CH$—$C_6H_{13}$, $LiC$≡$C$—$C_{19}H_{39}$, $LiCH(CH_3)_2$ $LiCH[CH(CH_3)_2]_2[C_6H_{11}C(CH_3)_3]$, $(CH_3)_3CCH$=$CHNa$, $LiCH_2C_6H_5$, $NaC_{10}H_7$, $Cd(C_7H_{15})_2$, $LiC_{30}H_{61}$, $NaC(C_6H_5)_3$, $LiCH(C_6H_5)_2$, $B(C_2H_5)_3$, $LiCH_2CH_2CH_2CH(C_5H_9)_2$, $NaCH(C_6H_5)_2$, $AlH_3$, $BH_3$, $AlH_2OCH_3$, $AlH_2OC_6H_{13}$, $AlH(OC_6H_5)_2$, $AlH(OC_{12}H_{25})_2$, $AlH(OC_4H_9)_2$, $BH(OC_2H_5)_2$, $AlH_2N(CH_3)_2$, $AlH[N(C_3H_7)_2]_2$, $AlH[N(C_6H_{11})_2]_2$, $AlHCl_2$, $AlHBr_2$, $Al(C_2H_5)_3$, $AlH(C_4H_9)_2$, $GaH(C_2H_5)_2$, $In(C_4H_9)_3$, $Zr(Cp)_2HCl$, $Ga(CH_3)_2Br$, $Ga(C_3H_7)_3$.

In addition, compounds $M'R$ may be derived by metalation of organic substrates having at least one metalatable hydrogen atom whose pKa is between 15 and 39 on the MSAD scale, ("Fundamentals of Carbanion Chemistry", D. J. Cram, Academic Press, New York, 1965, p. 19) by using LiR and NaR compounds in which the pKa of HR is higher than that of the organic substrate to be metalated. Suitable nonlimiting examples of such substrates include

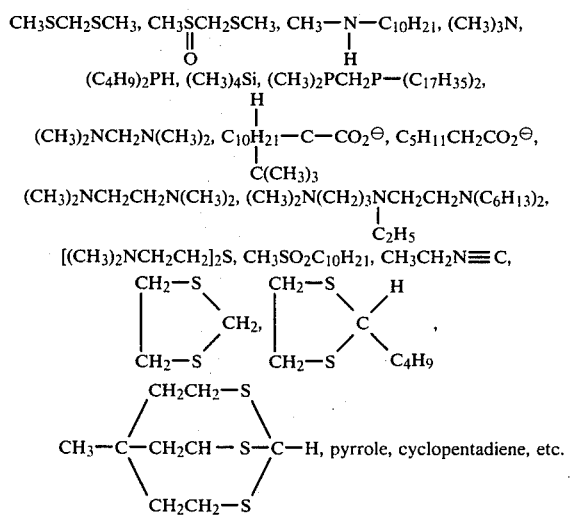

Suitable examples of compounds having the formula $M'H_mR_nX_p$ wherein m=o include $CH_3MgCl$, $C_6H_5MgOCH_3$, $(CH_3)_2CHBeSC_2H_5$, $CH_3ZnSCH_3$, $C_{10}H_{21}CdOC_{10}H_{21}$, $C_6H_{11}MgBr$, $C_3H_7MgN(CH_3)_2$, $C_4H_9MgI$, $C_4H_9MgBr$, $C_5H_{11}CdBr$, $C_6H_{13}BeOC_6H_5$, $C_6H_5CuI$, $C_6H_5CuOC_2H_5$, $CH_3MgSCH_3$, $CH_3ZnSC_{12}H_{25}$, $C_6H_5MgOC_6H_{11}$,

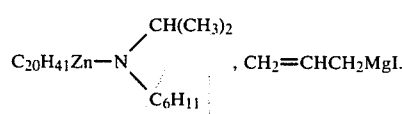

Preferred optically active chelating tertiary amino amides are those having the above formulas in which $R_1$ is a $C_1$ to $C_{20}$ hydrocarbyl radical; $R_2$, $R_3$, $R_4$, and $R_5$ are the same or different alkyl radicals of 1 to 4 carbon atoms inclusive; A is selected from the group consisting of a nonreactive group containing 2 to 3 methylenic radicals having 1 to 3 monovalent substituents containing 1 to 10 carbon atoms or a cyclohexyl radical and its lower alkyl or naphthenic derivatives wherein said radical is attached to the nitrogen atoms in a trans fashion at adjacent positions on the ring such that the chelating tertiary amino amide does not have a center, plane or alternating axis of symmetry.

Particularly preferred optically active chelating tertiary amino amides of this invention are those diamino and triamino compounds having the above formulas in which $R_1$ is a $C_1$ to $C_{20}$ hydrocarbyl radical; $R_2$, $R_3$, $R_4$ and $R_5$ are methyl groups; A is selected from the group consisting of a nonreactive group containing 2 methylenic radicals having 1 to 2 monovalent substituents containing 1 to 10 carbon atoms or a cyclohexyl radical and its lower alkyl or naphthenic derivatives, wherein said radical is attached to the nitrogen atoms in a trans fashion, at adjacent positions on the ring such that the chelating tertiary amino amide does not have a center, plane or alternating axis of symmetry.

Furthermore, in all of the above formulas, one or more R groups may contain resolved chiral centers. In such cases, it is not essential that Group A also be chiral and optically active. Thus, chelating tertiary amino amides having the structures:

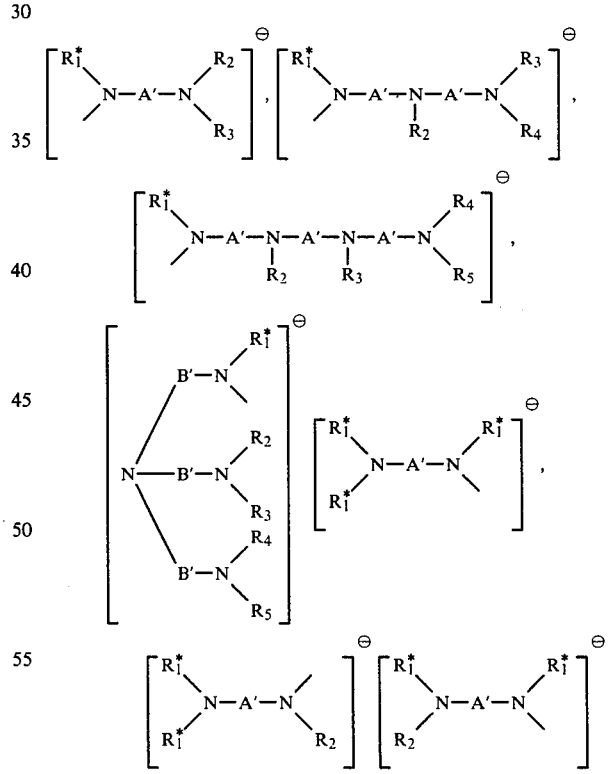

are claimed as part of this invention wherein $R_1$* is a $C_4$ to $C_{20}$ hydrocarbyl group containing at least one resolved asymmetric carbon atom which is removed no more than 4 carbon atoms from the nitrogen atom; A' is a nonreactive group containing 2 to 3 methylene radicals or a cycloaliphatic radical and their lower alkyl or naphthenic derivatives having ring structures containing 5 to 7 members wherein said radicals are attached to the nitrogen atoms at adjacent positions on the rings; B' is a nonreactive group containing 2 to 3 methylene radicals; $R_2$–$R_5$ are as defined previously. Obviously, the chelating tertiary amino amide may contain more than one optically active R group as long as it does not contain a center, plane or alternating axis of symmetry. In the preferred structures, the non-optically active R groups are methyl groups.

Suitable nonlimiting examples of optically active chelating tertiary amino amides [Chel*N]⊖, claimed in this invention include compounds having the following structures:

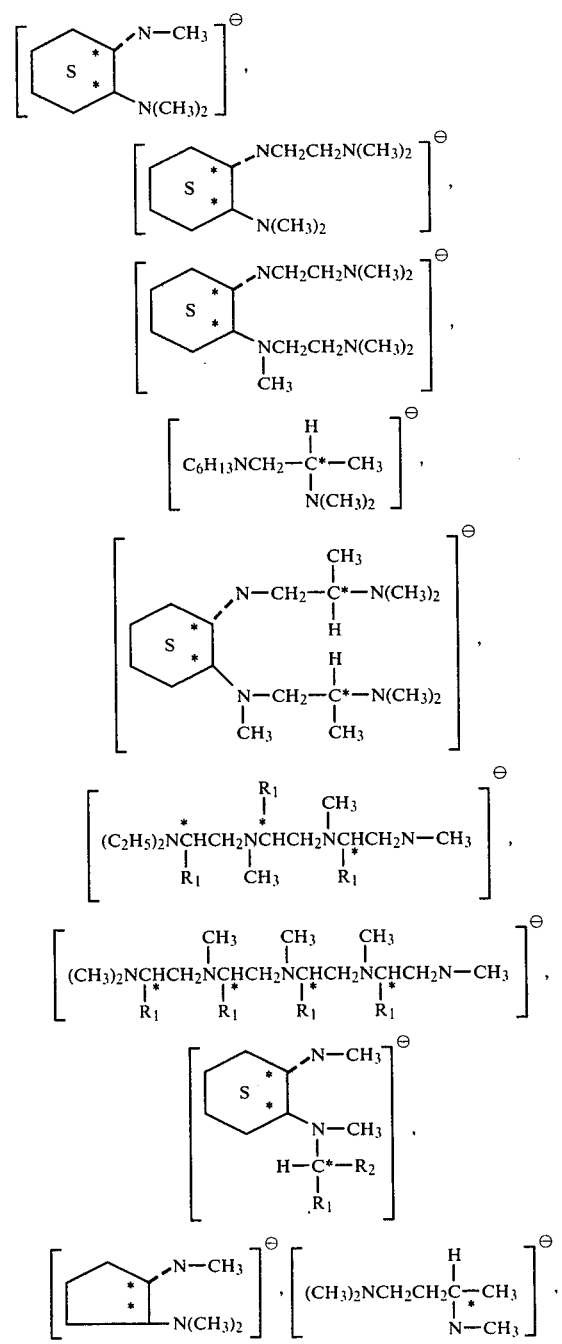

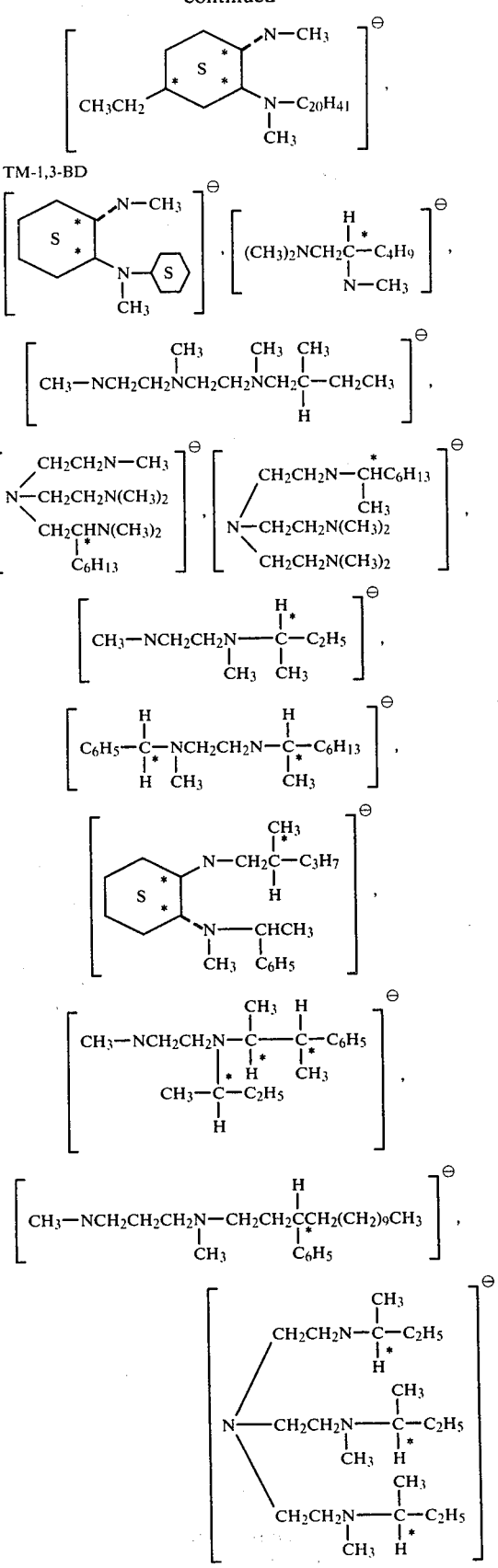

Some nonlimiting examples of the types of optically active chelating tertiary amino metal amides of this invention are as follows:

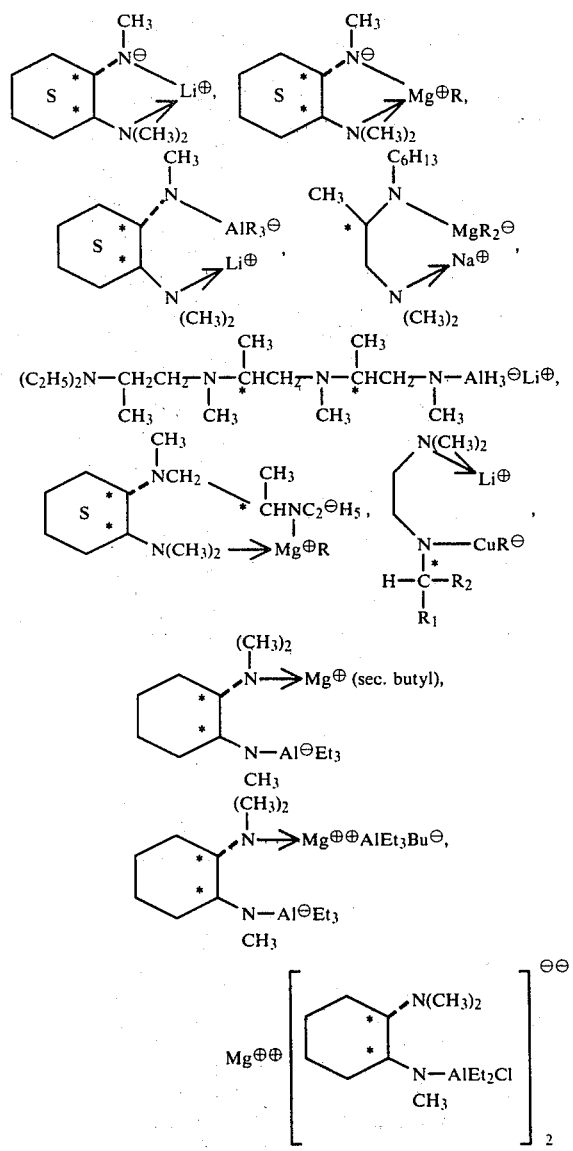

The optically active chelating tertiary amino metal amides derived from trans-1,2 cyclohexane diamine (trans-DACH) as defined hereinabove are prepared from optically active DACH which is obtained by the optical resolution of racemic trans-DACH via its netural d-tartrate salt to initially afford (−)DACH. This optical resolution is known in the prior art [R. G. Asperger and C. F. Liu, "Inorganic Chemistry" 4, page 1492 (1965)], (−)DACH may then be methylated via the Eschweiler-Clarke procedure (H. T. Clarke, H. B. Gillespie and S. Z. Weisshaus, "J. Am. Chem. Soc.", 55, 4571 (1933) to prepare (−) N,N,N′,N′—tetramethylcyclohexane diamine ((−)-TMCHD).

From the mother liquors remaining after the separation of the neutral d-tartrate of (−)DACH, it is known in the art (F. M. Jager and L. Bijkerk, "Proc. Akad. Sci. of Amsterdam" 40, P12 (1937)) that the acid d-tartrate of (+)DACH may be precipitated by adding an additional equivalent of d-tartaric acid and ethanol. The acid d-tartrate of (+)DACH is converted to (+)-DACH.2HCl and the latter is fractionally crystallized from water to obtain (+)DACH.2HCl of greater optical purity. This process is very inefficient and optical yields are quite low.

It has been found that (+)DACH of high optical purity and high chemical purity may be obtained from low optical purity and low chemical purity DACH recovered from the basicified mother liquors left after separation of (−)DACH d-tartrate by carefully controlled fractional crystallization of said impure (+)DACH either neat or from hydrocarbon solution.

Furthermore, it has been found that (+)TMCHD of very high chemical purity and high optical purity may be prepared from said impure (+)-DACH by methylation (loc.cit.) of the whole followed by fractional crystallization of a (+)TMCHD inorganic lithium salt chelate from hydrocarbon medium. This process is far more efficient and affords improved optical and chemical yields of (+)TMCHD over the method of securing (+)DACH via its acid d-tartrate followed by dihydrochloride fractional crystallization and subsequent methylation.

The optically active chelates as defined hereinabove which are not derived from DACH are prepared from other suitable optically active polyamines. For example, it is known in the prior art [Francis P. Dwyer, Francis L. Garvan and Albert Shulman, "J. Am. Chem. Soc." 81, 290 (1959)] that racemic 1,2-propanediamine may be resolved into its optical antipodes using d-tartaric acid as the resolving agent. Both the (+) and (−)-isomers may be obtained which could then be methylated via the Eschweiler-Clarke reaction to afford TM-1, 2-PD (N,N,N′,N′-tetramethyl-1,2-propanediamine).

Higher homologs, i.e., triamines could be also prepared using optically active 1,2-propanediamine as starting material. Thus, reaction of the diamine with one equivalent of n-butyllithium to give the mono-lithioamide followed by reaction of the latter with $(CH_3)_2NCH_2CH_2Cl$ would give

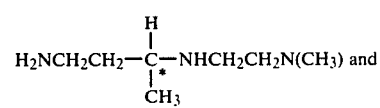

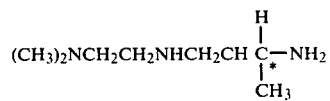

which could then be methylated via the Eschweiler-Clarke reaction.

Alternatively, optically active 1,2-propanediamine or its conjugated base could be reacted with an optically active organic compound containing a displaceable group, such as halide or tosylate, to yield a product having an additional asymmetric center attached to nitrogen. An example of such a reaction is shown below:

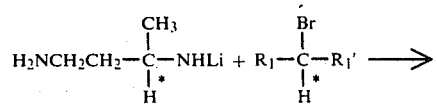

-continued

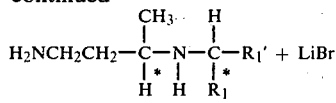

This process could be repeated to introduce additional asymmetric centers into a chelating polyamine. Finally, the Eschweiler-Clarke reaction would afford the N-peralkylated optically active chelating polyamines and removal of one methyl group therefrom would yield a "nor-methyl" compound which upon metalation with MR gives [Chel*N]$^-$M$^+$ of the subject invention. Extensions and variations of the above schemes are apparent to one skilled in the art.

The molar ratio of [Chel*N]$^\ominus$M$^+$ to M'H$_m$R$_n$X$_p$ may be in the range of about 10:1 to 1:10, preferably 2:1 to 1:2 and most preferably at 1:1.

An electrophilic reaction on unsaturated substrates can be depicted schematically by the reaction of an optically active chelate compound [Chel*-N]$^\ominus$M$^\oplus$M'H$_m$R$_n$X$_p$ with a prochiral unsaturated compound.

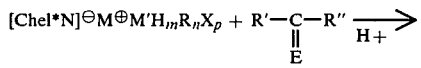

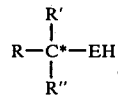

wherein M', R, X, m, n and p are as defined previously. The structures of R' and R" are not critical as long as they are different from each other before and after reaction with the optically active chelate compounds. R' and R" are groups such as hydrogen, alkyl, aryl, aralkyl, alkaryl, naphthenic, etc., and may contain one or more functional groups such as olefin, acetylene, ether, thioether, primary secondary or tertiary amine, imine, amide, ketal, acetal, hydroxyl, thiol, nitrile, sulfoxide, sulfone, nitro, ester, carboxyl, halide, phosphine, silane, germane, stannane and metallocene. It is understood that Mg (++) [Chel N]$_2^\ominus$ wherein [Chel N]$^\ominus$ is not $$\left[ \begin{array}{c} CH_3 \\ \diagdown \\ CH_3 \end{array} N-A-N \begin{array}{c} CH_3 \\ \diagup \\ \diagdown CH_3 \end{array} \right]^\ominus,$$

[Chel N]$^\ominus$M$^\oplus$—M'H$_m$R$_n$X$_p$, Z Mg$^\oplus$[Chel N—M'H$_m$R$_n$X$_p$]$^\ominus$, Mg $^{++}$ [Chel N—M'H$_m$R$_n$X$_p$]$^\ominus$[M'H$_m$R$_n$X$_p$Z]$^\ominus$, Chel N—Mg$^\oplus$[M'H$_m$R$_n$X$_p$Z]$^\ominus$ and Mg (++) [Chel N—M'H$_m$R$_n$X$_p$]$_2^\ominus$ may react with some functional groups in R' and R" as long as the reaction does not produce two identical groups attached to the symmetric atom or prevent reaction at the prochiral center when excess of the above chelating tertiary amino metal amide is present. Each R' and R" group will normally contain less than about 30 carbon atoms and may be connected such as to form ring structures as long as the substrate is a prochiral compound. E equals O, S or a monosubstituted nitrogen radical. Thus, the unsaturated prochiral functional groups are carbonyl, thiocarbonyl or unsaturated imino. Suitable unsaturated prochiral substrates include compounds having functional groups such as aldehydes, ketones, $\alpha,\beta$-unsaturated carbonyl compounds such as RCH=CH—CO$_2$R' or RCH=CH—CONR'$_2$, thioaldehydes, thioketones, imines, oximes, hydrazones, semicarbazides, osazones, and related compounds. Preferred functional groups in the prochiral substrate are selected from the group consisting of aldehydes, ketones, imines, oximes and hydrazones. Since R' and R" groups are not critical, some representative, nonlimiting examples are listed for illustrative purposes: benzaldehyde, acetophenone, benzil mono-oxime, butyraldehyde, 2-octanone, octadecyl naphthyl ketone, ethyl cyclohexyl ketone, methyl crotonate, furaldehyde, phenylsulfonylacetone, $\beta$-acetyl-pyridine, thiobenzaldehyde, phenylcyclohexyl, thioketone, N-phenylbenzaldimine, phenylacetaldimine, methyl 2-butyl ketoneoxime, ethylpyruvate phenyl hydrazone, glucose phenylosazone, 3-hydroxypropyl methyl ketone, 2-ethoxyethyl methyl ketone, o-dimethylaminobenzaldehyde, 1-ferrocenyl-4-pentanone, CH$_3$SO$_2$CH$_2$CH$_2$COCH$_3$, (CH$_3$)$_2$PCH$_2$CH$_2$CH$_2$CH$_2$CH(CH$_3$)-COC$_2$H$_5$, ClCH$_2$CH$_2$CH$_2$COCH$_3$, (CH$_3$)$_3$SiCH$_2$CH$_2$COCH$_3$, (CH$_3$)$_3$SiCOC$_6$H$_5$, (CH$_3$)$_3$GeCH$_2$CH$_2$COCH$_3$, (CH$_3$)$_3$SnCH$_2$CH$_2$COCH$_3$, C$_6$H$_5$COCO$_2$H, CH$_3$SCH$_2$CH$_2$COC$_6$H$_5$, CH$_2$=CHCH$_2$CH$_2$CH$_2$COC$_6$H$_{11}$, CH$_3$C≡CCH$_2$CH$_2$—COCH(CH$_3$)$_2$, $$\underset{\underset{N-C_{10}H_{21}}{\|}}{C_6H_5CCH_3}, \quad \underset{\underset{NCH_3}{\|}}{CH_3CCH_2CH_2SC_6H_4-p-CH_3},$$

$$p\text{-ClC}_6H_4CSCH_3, \quad \underset{\underset{SH}{|}}{CH_3CHCH_2CH_2CCH_3},\underset{\underset{O}{\|}}{}$$

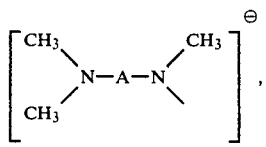

Any inert solvent may be used for reaction of the optically active chelates with unsaturated prochiral substrates.

This reaction can be carried out in the presence of any solvent which is inert to [Chel*N]$^\ominus$M$^\oplus$, [Chel*-N]$^\ominus$M$^\oplus$—M'H$_m$R$_n$X$_p$, Z Mg$^\oplus$[Chel*N—M'H$_m$R$_n$X$_p$]$^\ominus$, Mg (++) [Chel*N—M'H$_m$R$_n$X$_p$]$^\ominus$—[M'H$_m$R$_n$X$_p$Z]$^\ominus$, Chel*N-Mg$^\oplus$[M'H$_m$R$_n$X$_p$Z]$^\ominus$, Mg (++) [Chel*-N—M'H$_m$R$_n$X$_p$]$_2^\ominus$, Mg (++) [Chel*N]$_2^\ominus$.

For example, aromatic hydrocarbons may be used except in those cases where the complex is reactive enough to metalate aromatic compounds. In those cases, saturated hydrocarbon solvents are preferred. The reaction can be run at any convenient temperature, i.e. from $-100°$ to $+100°$ C. but generally lower temperatures, ranging from $-80°$ to $30°$ C. are preferred.

The mole ratio of the optically active chelate to the prochiral substrate may be in the range of 10:1 to 1:10, preferably 2:1 to 1:2 and most preferably about 1:1 based on the number of reactive groups in the optically active chelate and in the prochiral substrate.

Other optically active chelates that may be employed in asymmetric synthesis of this invention include those in which the anion has the formula $$\underset{\underset{O}{\|}}{R-S-CH-SR} \quad \text{and} \quad (RS)_3C^-.$$

Products containing these radicals may be converted to aldehydes and acids. Hence a synthesis of optically active α-amino acids can be formulated:

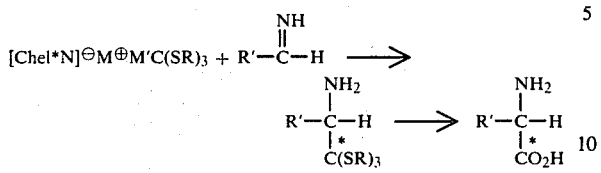

By means of this invention, well known compounds having medicinal value or other important biological properties may be prepared in optically active forms by choice of the proper prochiral substrate. Such compounds include d-desoxyephedrine, 1-ephedrine, L-DOPA, 1-epinephrine, 1-menthol, mephenesin [3-(o-tolyloxy)-1,2-propanediol], certain sugar stereoisomers, alanine, phenylalanine and tyrosine, etc.

Another aspect of this invention relates to the use of the optically active chelated complex metal hydrides for preparation of optically active sulfoxides and phosphine oxides and phosphines via partial reduction of such chiral compounds. This aspect of the invention is illustrated by the following equations:

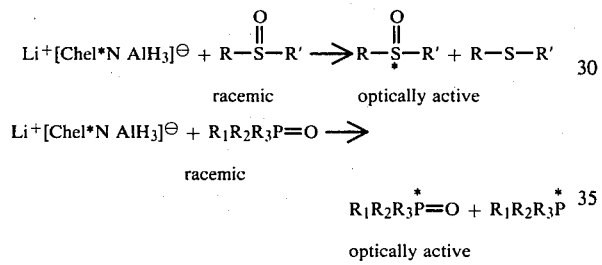

In practicing this aspect of the present invention, the mole ratio of [Chel*N]⊖LiAlH$_3$ to racemic sulfoxide or phosphine oxide is chosen so as to avoid complete reduction. Generally, the reduction is carried to from about 10% to 90% of completion, preferably to about 50% of completion and the recovered unreduced phosphine oxide or sulfoxide is found to be optically active.

Still another aspect of this invention is the use of optically active organolithium chelates [Chel*-N]⊖Li⊕R$_6$, to metalate polymers and then to react the optionally active chelated metalated polymer species with a prochiral substrate thereby yielding polymers with optically active functional groups. The general polymer metalation process is the subject of U.S. Pat. No. 3,769,345. This aspect of the invention is illustrated as follows for polystyrene:

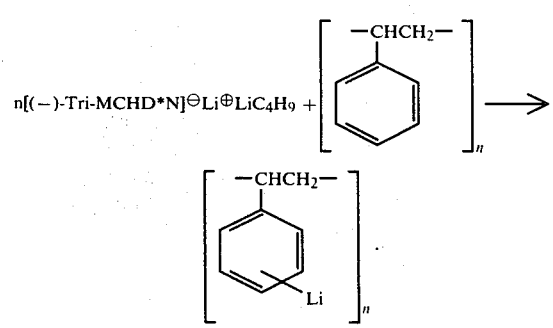

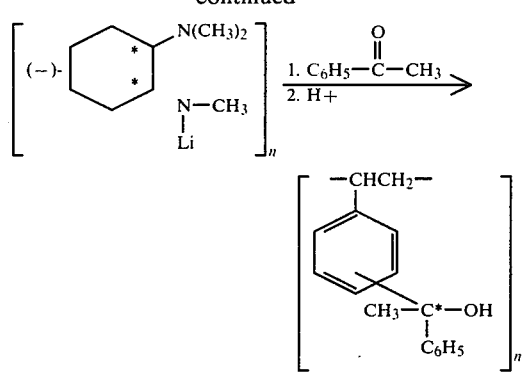

The mole ratio of the optically active metalating agent to the polymer monomer unit may vary widely depending upon the degree of functionalization desired, but will normally be about 1:1000 to 1:1. $R_6$ is selected from the group consisting of $C_1$ to $C_{20}$ alkyl, aryl, aralkyl, naphthenyl or alkaryl radicals. All of the above reactions may be run with racemic components to yield racemic products.

This invention is illustrated by the following examples:

EXAMPLE I

Preparation of Optically Active (+) and (−)—N,N,N'N'-Tetramethyl-1,2-cyclohexanediamine ((+)- and (−)-TMCHD)

To 2 liters of water was added 333.3 g (2.92 moles) of impure 1,2-diaminocyclohexane (DACH) and the solution was warmed to about 60° C. To the warm solution was added 440 g (2.92 moles) of d-tartaric acid in small portions. An additional 920 ml of water was added as the d-tartaric acid was being added. The temperature of the final reaction mixture was 90° C. To the hot homogeneous solution was added a few seed crystals of (−)-DACH tartrate and the whole was allowed to slowly cool to room temperature, stand at room temperature for 2 days and was then cooled to 0°–5° C. for two more days.

Two additional batches were prepared exactly as described above. All three batches of DACH tartrate were then filtered and the residue was dried, wt. 542 gm. (crop 1) total.

The mother liquor from the filtration was concentrated in a rotary evaporator until the total volume was about 4.5 liters and additional tartrate salt deposited which was recovered by filtration, wt. 267 g (crop 2). An additional crop of tartrate salt separated upon further concentration of the mother liquor to about 2 liters, wt. 180 g (crop 3).

Crop 1 DACH tartrate, wt. 541.5 g, and one liter of water were placed in a two liter continuous extraction apparatus. Enough 50% NaOH solution was added to make the mixture strongly basic and the mixture was extracted with benzene until no more DACH was found in the extract. The benzene was removed from the crude optionally active DACH and the latter was distilled, b.p. 71–73/8 mm, wt. 216 g [α]$_{589}^{25}$-40.3° (C=5.23, benzene) which corresponds to 97% optical purity. This value was determined by converting (−)-DACH.2HCl of [α]$_{589}^{23}$=−15.6° (C, 0.2 g per ml H$_2$O), (lit. R. G. Asperger and C. F. Liu, "Inorganic Chemistry", 4 1493 (1965), [α]589=−15.8° (C, 0.2 g per ml H₂O)), to the free amine and then determining that optically pure (−)DACH has a rotation of $[\alpha]_{589}^{25} = -41.4°$ (C=5, benzene). (−)DACH was found to be rather insensitive in its specific rotation to concentration changes in benzene over the range C=5.871 to C=4.00 grams per 100 ml: $[\alpha]_{589}^{25} = -41.0°$ (C=5.871); $[\alpha]_{589}^{25} = -42.0°$ (C=4.00).

Cut-back of Crop 2 DACH tartrate in the same manner as Crop 1 gave 70 g of (−)DACH having $[\alpha]_{589}^{25} = -33.6°$ (C=4.92, benzene) which corresponds to 80.6% optical purity.

The mother liquor remaining after Crop 3 DACH tartrate separated was treated as described for the Crop 1 tartrate and 540 g of distilled product was obtained which displayed $[\alpha]_{589}^{25} = +20.3°$ which corresponds to 48.7% optical purity assuming that the product was chemically pure. (That the recovered (+)-DACH was not chemically pure, even though the GC of the material on a Carbowax 20M-KOH column showed only one peak, will be shown below).

Optically pure (+) or (−)-DACH has a melting point of 43°-44° C. while racemate is a liquid. Thus, trans-1,2-diaminocyclohexane is a racemic mixture and partially optically pure material may be made more nearly optically pure by careful fractional crystallization of the neat material from a melt. (For a discussion of the different types of behavior of chiral compounds see Stereochemistry of "Carbon Compounds" by Ernest L. Eliel, McGraw-Hill, Inc., New York 1962, Chapters 1 and 2).

The procedure of upgrading partially optically pure DACH via fractional crystallization from the melt or from hydrocarbon solution is a very facile means of obtaining (+)-DACH of high optical purity. This procedure is considerably superior to that of the literature (R. G. Asperger and C. F. Liu, "Inorganic Chemistry" 4 1492 (1965) which involves forming the bitartrate of (+)-DACH after separation of ethanol to the hot bitartrate solution, converting the (+)-DACH bitartrate to the dihydrochloride, fractionally crystallizing the dihydrochloride from water and finally hand picking the optically active (+)-DACH dihydrochloride crystals from the featherlike aggregates of racemic salt.

The fractional crystallization technique was applied to 540 g of (+)-DACH having $[\alpha]_{589}^{25} + 20.3°$ (C 5.05 benzene). The material was placed in a Schlenk tube which was placed in a constant temperature bath at 20° C. Over a period of 19 days the temperature of the bath was slowly lowered to 9° C. as a crop of crystals grew. After this period of time the Schlenk tube was inverted and the solids were filtered from the mother liquor. The arm of the Schlenk tube containing the solids was heated and the molten (+)-DACH was removed from the tube with a pipette. It displayed $[\alpha]_{589}^{25} + 38.7°$ (C 5.32 benzene) which is 94% optically pure: 137.9 g was obtained. The mother liquor, $[\alpha]_{589}^{25} + 13.4°$ (C 5.03), 331 g was charged into a new Schlenk tube and put back into the bath at 9° C. Over a period of 18 days the bath temperature was lowered to −3° C. as a second crop of crystals formed which were recovered and melted. This material displayed $[\alpha]_{589}^{25} + 36.2°$ (C 5.23 benzene) or 87.5% optical purity, wt. 56.2 g. The mother liquor displayed $[\alpha]_{589}^{25} + 8.22°$ (C 5.09 benzene).

Further cooling of the mother liquor did not afford additional (+)-DACH crystals. This behavior was strange because a prior batch of (+)-DACH of only +4.7° continued to deposit crystals when cooled as low as −5° C. It was concluded that most probably the (+)-DACH of +8.22° was impure and that the impurities were preventing the excess (+)-antipode from separating.

Therefore, 111 g (0.97 mole) of the (+)-DACH of $[\alpha]_{589}^{25} + 8.22°$ was methylated via the Eschweiler-Clarke procedure (H. T. Clarke, H. B. Gillespie and S. Z. Weisshaus, "J. Amer. Chem. Soc." 55, 4571 (1933)) using 545 ml of 90% formic acid and 354 ml of 40% aqueous formaldehyde. The resulting (+)-trans-N,N,N',N'-tetramethyl-1,2-cyclohexanediamine ((+)-TMCHD) was found to have $[\alpha]_{589}^{25} + 3.97°$ (neat) or 19.8% optical purity and 70.7% chemical purity by VPC analysis, wt. 153.3 g bp 70°-73° C. @ 4 mm. (Optically pure TMCHD has $[\alpha]_{589}^{25} \pm 17.2°$ (neat) d=0.888 @ 25° C. $[\alpha]_{589}^{25} \pm 52.9°$ (C 5.51, 95% ethanol) and $[\alpha]_{589}^{25} \pm 20.0°$ (C 5.06 benzene.))

To 150 g (~231 mmoles) of the impure (+)-TMCHD of $[\alpha]_{589}^{25} + 3.97°$ (neat) was added 50 ml of benzene and 20 g (231 mmoles) of LiBr. Then an additional 50 ml of benzene was added and the clear homogeneous solution was allowed to stand at room temperature for 13 days and a crop of crystals separated which were recovered by filtration and washed with 25 ml of pentane, wt. 45.7 g. The (+)-TMCHD was recovered from the LiBr chelate by dissolving the latter in water, making the solution strongly basic with NaOH and extracting the mixture with hexane. The recovered (+)-TMCHD displayed $[\alpha]_{589}^{25} + 15.45°$ (C 5.60 benzene) or 77.2% optically pure and was 99+% pure by VPC analysis. Thus via chelation with lithium salts chemically and optically impure TMCHD may be upgraded in both chemical and optical purity in a single step process.

EXAMPLE 2

A 25 g (219 mmoles) portion of 96% optically pure (−)-trans-1,2-diaminocyclohexane ((−)-DACH), prepared as described in Example I was dissolved in 625 ml of acetonitrile. Benzyl chloride, 41.57 g (328.3 mmoles) was dissolved in enough of a separate portion of acetonitrile to make 250 ml of solution. A solution of 26.26 g (328.3 mmole) of NaOH was also prepared in enough water to make 125 ml of solution.

The (−)-DACH solution was heated to 60° C. and aliquots of the benzyl chloride and sodium hydroxide solutions were added alternately with stirring so as to keep the reaction mixture basic. Addition of the two solutions required 12 hours after which the reaction mixture was refluxed 6 hours.

The reaction mixture was evaporated on a rotary evaporator and the residue was methylated by the Eschweiler-Clarke procedure using 125 ml of 90% formic acid and 67 ml of 40% aqueous formaldehyde. A 45 ml portion of conc. HCl was added to the methylation reaction mixture and the whole was stripped on a rotary evaporator. The residue was made strongly basic and extracted with hexane. The hexane extract was dried (K₂CO₃) and evaporated leaving 59 g of crude liquid product.

The crude product, 59 g, was added to 75.2 g of pentane along with 8.44 (199.1 mmoles) of LiCl and the hetrogeneous mixture was stirred for 3 days at room temp. and was then filtered. The filtration residue weighed 9.4 g. The filtrate was concentrated and the residue, 59.9 g, was combined with the product of a similar run (19.2 g) and the whole was distilled. A fraction bp 90°-92° @ 0.005 mm, wt. 17.8 g, was collected. A considerable amount of residue remained in the distillation pot. The distilled product was found by VPC analysis to contain 2.2% trans-N,N,N',N'-tetramethylcyclohexanediamine (trans-TMCHD) and 97.8% trans-N,N,N'-trimethyl-N'-benzylcyclohexanediamine. The NMR spectrum of the product was consistant with the latter structure.

A 3.03 g (12.5 mmoles) portion of the trans-N,N,N'-trimethyl-N'-benzylcyclohexanediamine was hydrogenated in 25 ml of glacial acetic acid @ 40 psig in a Parr hydrogenation apparatus. The catalyst employed was a palladium hydroxide on Darco G-60 carbon catalyst prepared according to *Reagents for Organic Synthesis* by M. Fieser and L. F. Fieser, John Wiley and Sons, New York, N.Y., 1967, p. 782. Hydrogenation appeared to be complete in about five minutes but was allowed to continue for 2.5 hours. The catalyst was removed by filtration and the filtrate was stripped le leaving a residue, wt. 3.9 g, which was methylated again using 7 ml of formic acid and 4.5 ml of formaldehyde. Work-up of the second methylation reaction afforded 1.20 g of distilled (−)-trans-TMCHD bp 66° C. @ 3.2 mm. which was found to be identical in all respects with a sample of (−)-trans-TMCHD prepared directly from (−)-trans-DACH. Both materials displayed $[\alpha]_{546}^{25} -22.6°$ (C, 5.00, benzene) within experimental error.

These results establish that an N-benzyl group may be removed from the nitrogen atom, leaving an -NH function in an optically active chelating polyamine substrate by hydrogenation using the Pd(OH)$_2$ catalyst without concomitant racemization or epimerization of a chiral center.

Having demonstrated that the benzyl group could be removed without racemization, an 8.26 g portion of (−)-trans-N,N,N'-trimethyl-N'-benzylcyclohexanediamine was hydrogenated in 50 ml of glacial CH$_3$CO$_2$H using 1 g of catalyst. Evaporation of CH$_3$CO$_2$H and addition of excess NaOH solution yielded (−)-trans-N,N,N'-trimethylcyclohexanediamine ((−)-Tri-MCHD), wt. 5.1 g. Another run gave 3.7 (−)-Tri-MCHD from 6.26 g of N-benzyl compound and the products were combined and distilled. A main cut bp 70.5°-72° C. @ 6 mm, wt. 7.4 g, was taken. VPC analysis indicated a purity of 98.0%, 0.3% solvent, 1.4% unknown and 0.2% TMCHD. The distilled product displayed $[\alpha]_{589}^{25} -89.3°$, $[\alpha]_{546}^{25} -104.4°$ and $[\alpha]_{365}^{25} -230.2°$ (C, 5.0, benzene). Analysis: theory, C, 69.17%; H, 12.90%; N, 17.93%; found C, 68.96%; H, 12.94%; N. 17.83%.

By the same procedure as described above other Chel*NH compounds may be prepared from other suitable optically active chelating polyamine starting materials.

EXAMPLE 3

A 294 milligram portion of (−)-Tri-MCHD, $[\alpha]_{589}^{25} -89.3°$ (C, 5.0, benzene) was dissolved in 10 ml of heptane and to the solution was added dropwise 2.2 ml of a 0.92 molar solution of n-butyl lithium in heptane. The solution was stirred for several hours and then the heptane was removed under reduced pressure leaving a white crystalline deposit, wt. 352 milligrams after vacuum drying. A 52 milligram portion of this product which is trans-N-lithio-N,N,N'-trimethylcyclohexanediamine was dissolved in 0.5 ml of benzene and analyzed by NMR. The three N-methyl groups gave three separate resonances (singlets). The compound displayed $[\alpha]_{589}^{25} -15.4°$, $[\alpha]_{578}^{25} -14.7°$, $[\alpha]_{546}^{25} -11.4°$ and $[\alpha]_{436}^{25} +53.2°$ (C, 5.22, benzene).

In a similar fashion compounds of the type [Chel*N]$^\ominus$M$^\oplus$ in which M is a different Group IA metal or Mg may be prepared by using a suitable Group IA or Mg organometallic reagent or hydride.

EXAMPLE 4

To a 1.56 g (10 mmole) portion of (−)-Tri-MCHD in 20 ml in toluene was added 0.38 g of LiAlH$_4$ and the mixture was stirred for 2 days as a slow gas evolution occurred. A portion of the mixture was filtered through a fitted disk and the clear solution was evaporated leaving a white crystalline deposit, wt. 0.8 g. which was

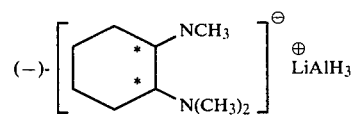

The NMR spectrum of the compound showed three separate singlets for the N-methyl groups.

EXAMPLE 5

To a 1.56 g (10 mmoles) portion of (−)-Tri-MCHD in 40 ml of toluene was added 0.38 g (10 mmoles) of Li AlH$_4$ and the mixture was stirred overnight. The mixture was cooled to −80° C. and a solution of 2.40 g (20 mmoles) of acetophenone in 10 ml of toluene was added over a period of ½ hour. The reaction mixture was maintained at −75° to −80° C. for an additional ½ hour and then allowed to warm to room temperature and was then stirred for 2.5 days. Ice was added followed by 80 ml of 1NHCl and the organic phase was separated, washed with satd. NaHCO$_3$ solution, washed with water, dried over Na$_2$SO$_4$ and the toluene was evaporated. The residue, wt. 2.24 g, by VPC analysis was 7.3% toluene, 47% acetophenone and 45% α-phenethyl alcohol and it displayed $[\alpha]_{589}^{25} -7.90°$ (C, 13.0, benzene).

A mixture of 0.2237 g of optically pure (+-α-phenethyl alcohol and 0.2604 g of acetophenone was prepared and examined at C=13.0 in benzene @ 589 mμ. The synthetic mixture displayed $[\alpha]_{589}^{25} +23.98°$. Thus the α-phenethyl alcohol produced in the above reduction of acetopheneone had an optical purity of 33%.

Therefore, the compounds of this invention having the structure [Chel*N]$^\ominus$M$^\oplus$M'H$_n$ are useful reagents for asymmetric syntheses.

EXAMPLE 6

One gram (6.2 mmoles) of (−)-N-lithio-N,N',N'-trimethylcyclohexanediamine was dissolved in 40 ml of toluene and 1.22 g (6.2 mmoles) of Al(n-C$_4$H$_9$)$_3$ was added as a solution in 15 ml of toluene. The mixture was stirred overnight and cooled to −75° to 31 80° C. Then a solution of 0.65 g (6.2 mmoles) of benzaldehyde in 15 ml of toluene was added gradually. The reaction mixture was subsequently treated as detailed in Example IV except that two acid washes were employed. The product 1-phenyl-1-pentanol, wt. 0.84 g, was found to have an optical purity of 18%; it was dextrorotory.

EXAMPLE 7

A run was made as described in Examples 5 and 6 employing 1 g (6.2 mmoles) of (−)-N-lithio-N,N',N'-trimethylcyclohexanediamine, 6.2 millimoles of Mg (n-C$_4$H$_9$)$_2$ and 0.65 g (6.2 mmoles) of benzaldehyde. The product 1-phenyl-1-pentanol, wt. 0.8 g., was found to have an optical purity of 22.5%; it was dextrorotory.

EXAMPLE 8

A run was made as described in Examples 5 and 6 employing 1 g (6.2 mmoles) of (−)-N-lithio-N,N,N-trimethylcyclohexanediamine, 1.11 g (6.2 mmole) of diphenyl magnesium and 0.53 g (6.2 mmoles) valeraldehyde. The product 1-phenyl-1-pentanol, wt. 0.8 g, was found to have an optical purity of 22.7%; it was levorotory.

EXAMPLE 9

A run was made as described in Examples 5 and 6 employing 0.97 g (6 mmole) of (−)-N-lithio-N,N,N-trimethylcyclohexanediamine, 6 mmoles of Zn(C$_2$H$_5$)$_2$ and 0.6 g (6 mmoles) of hexanal. The product, wt. 0.6 g, which by VPC analysis was 74.1% 3-octanol, 14.8% toluene and 11.9% hexanal displayed $[\alpha]_{435}^{25}$ −0.28° (C, 13.35, benzene).

Furthermore, the M'H$_m$R$_n$X$_p$ component in this reaction may be other reactive organometals of Group II A and B. Specifically, Be, Mg and Cd organometallics may be used.

EXAMPLE 10

A 103.1 g (1.0 mole) portion of diethylenetriamine was added to 1500 ml of benzene in a 3-necked 3-liter flask equipped with a paddle stirrer, thermometer and nitrogen inlet. Butyl lithium, 450 ml (1.05 mole) in hexane solution, was added dropwise over 1.5 hours and the reaction mixture was kept below 40° C. A solution of 126.6 g (1 mole) of a -chlorotoluene in enough benzene to make a total volume of 315 ml was added dropwise over a 1 hour period while the reaction mixture was maintained at 38°–40° C. Water, 200 ml, was added with stirring, the layers were separated, and the organic phase was stripped on a rotary evaporator with water aspirator vacuum leaving a residue of 340 g.

The residue was added to 835 ml of 90% formic acid and 475 ml of 37% aqueous formaldehyde was added dropwise at 90° C. The reaction mixture was refluxed for 43 hours, 91 ml of 1.6 molar H$_2$SO$_4$ was added and the whole was stripped on the rotary evaporator with a bath temperature of 70° C. To the residue was added 100 ml and the mixture was stripped again. To this residue was again added 100 ml of water and the mixture was stripped again. Then the residue was made basic with excess NaOH solution and the liberated amine product was recovered by extraction with six 120 ml portions of hexane. The hexane solution was dried over MgSO$_4$ and stripped on a rotary evaporator leaving a residue of 235.5 g which was distilled. A forerun of 100 g bp 55°–84° C. at 2.7 to 0.07 mm was removed first in several cuts and then the higher boiling residue was distilled at 0.005 mm giving a cut of 10.8 g. A pot residue of 107.8 g remained.

The high vacuum cut of 10.8 g and the last two cuts of the lower vacuum distillation, wt. 1.7 g and 7.8 g respectively were combined and 19.6 g of the combined material was added to 150 ml of glacial acetic acid along with 1 g of a palladium hydroxide on carbon hydrogenation catalyst (prepared according to Fieser and Fieser, Reagents for Organic Synthesis, Vol. I, John Wiley and Sons, 1967, p 782). The mixture was hydrogenated in a Parr shaker @ 40 psi H$_2$ pressure for a day. The catalyst was removed by filtration and the acetic acid was evaporated under vacuum. The residue was dissolved in water, made basic with excess NaOH solution and extracted with four 35 ml portions of hexane. The hexane solution was dried over MgSO$_4$ and evaporated yielding a crude product weighing 10.0 g which was distilled yielding 7.9 g of product Bp 54°–55.5° C. at 2.5 mm. This product was N,N',N''N''-tertramethyldiethylenetriamine (normethyl-PMDT): analysis, theory C, 60.33%; H, 13.29%; N, 26.38%; found C, 60.69%; H, 12.97%; N, 26.46%.

Other normethyl chelating agents may be made by the same process. For example, normethyl HMTT may be prepared from triethylenetetramine and normethyl-iso-HMTT may be prepared from tris-$\beta$-aminoethyl)amine.

EXAMPLE 11

N,N,N',N'-tetramethyl-trans-1,2-cyclohexanediamene (trans-TMCHD), 89.6 g (0.53 mole) was dissolved in 1500 ml of toluene. A 121.1 g (0.57 mole) portion of $\beta$, $\beta$,$\beta$-trichloroethyl chloroformate was diluted to 500 ml with toluene and the latter solution was added dropwise with stirring to the trans-TMCHD solution over a 1-hour period while the reaction mixture was maintained at 0° C. during the addition and for 4 hours afterward. The reaction mixture was allowed to warm to room temperature overnight and the white slurry was then heated with stirring to 89° C. for 2 hours. The cooled reaction mixture was filtered removing 6.1 g of solids and the filtrate was evaporated yielding 217.8 g of clear deep-yellow liquid. The latter was dissolved in 1300 ml of glacial acetic acid and to the stirred solution was added 128 g of zinc dust in small portions while the reaction mixture was maintained at 25° C. with ice-bath cooling as required. Zinc dust addition required 1 hour and the reaction mixture was stirred an additional 4 hours at 25° C. and then filtered through a celite pad. The filter cake was washed with seven 100 ml portions of hot water. The combined filtrate and water washings were stripped and the residue, wt 290 g, was dissolved in water and made basic with excess NaOH solution. The product was recovered by extraction with six 100 ml portions of hexane, dried over MgSO$_4$ and stripped on a rotary evaporator leaving a residue wt. 96.5 g, which was distilled. A fraction Bp 64.5°–67.5° C. @ 4.5 mm was collected, wt. 67.9 g, which was 97% pure by VPC analysis. A pot residue of 12.1 g remained. The product was N,N,N'-trimethylcyclohexanediamine (Tri-MCHD). Analysis: theory for C$_9$H$_{20}$N$_2$ C, 69.17%; H, 12.90%; N, 17.93%. Found C, 69.17%; H. 12.03%; N, 17.90%. Mass spectral analysis gave a parent ion of MW=156. The yield of Tri-MCHD from TMCHD using this procedure was 82.3%.

EXAMPLE 12

A 1.10 g (7 mmole) portion of (−)-N,N,N'-trimethyl-cyclohexanediamine ((−)-Tri-MCHD), $[\alpha]_{589}^{25}$ −90.7° (C, 5.00, benzene), was dissolved in 22 ml of hexane and 7.44 mmoles of LiC$_4$H$_9$ solution in hexane was added dropwise with stirring over a 5 minute period at 25° C. To this solution was added 7 mmoles of 1-hexyne which reacted to form the chelate (−)-Tri-MCHD.LiC≡CC$_4$H$_9$. The reaction mixture was cooled to −80° C. and 0.75 g (7.1 mmoles) of benzaldehyde was added with stirring. The reaction mixture was held at −75° to −80° C. for 20 min. and then allowed to warm to room temperature over 75 minutes. It was then hydrolyzed by two extractions with 25 ml portions of 4 normal ice-cold acetic acid, washed with 25 ml of sat. NaHCO$_3$ solution, washed with 25 ml of water and the separated organic phase was dried over MgSO$_4$. The hexane solvent was stripped and the residue was heated for 45 min. at 50° C. under 0.7 mm vacuum, wt. 1.2 g. VPC analysis of the product indicated it to be 95% pure and not to contain any (−)-Tri-MCHD. The product displayed $[\alpha]_{589}^{25} -1.56°$, $[\alpha]_{436}^{25} -3.53°$ (C, 14.3, benzene). The product was:

$$C_6H_5-\underset{\underset{H}{|}}{\overset{\overset{OH}{|}}{C}}-C\equiv C-C_4H_9$$

as determined by mass spectral analysis (parent ion at MW=188) IR and NMR analysis and elemental analysis; theory for C$_{13}$H$_{16}$O C, 82.93%; H, 8.57%; found C, 83.75%; H, 8.54%.

The Example demonstrates that (−)-N'-lithio-N,N,N'-trimethylcyclohexanediamine ((−)-lithio-Tri-MCHD) may be used as an intermediate in the preparation of optically active alkynal lithium chelates and that the latter react with prochiral carbonyl substrates yielding optically active propargyl alcohols. Racemic Tri-MCHD may be similarly employed to synthesize racemic propargyl alcohols.

EXAMPLE 13

A 1.10 g (7 mmole) portion of racemic Tri-MCHD was dissolved in 22 ml of hexane and to the stirred solution under nitrogen was added 7.4 mmoles of C$_4$H$_9$Li solution in hexane at room temperature over a five minute period. After 20 minutes 7 mmoles of 1-hexyne as a 1 molar solution in heptane was added dropwise at room temperature and the mixture became turbid. After an additional 30 minutes the reaction mixture was cooled to −80° C. and 0.74 g (7 mmoles) of benzaldehyde was added. The stirred reaction mixture was maintained at −80° to −75° C. for 20 minutes and then allowed to warm to room temperature over 1.5 hours. The mixture was then hydrolyzed with 25 ml of cold 4 N acetic acid. The organic phase was extracted a second time with another 25 ml portion of cold 4 N acetic acid, once with 25 ml of saturated NaHCO$_3$ solution, once with 25 ml of H$_2$O and then dried over anhydrous MgSO$_4$. Evaporation of solvent gave 1.3 g of product which was 1-phenyl-2-heptyne-1-ol.

EXAMPLE 14

The procedure detailed in Example 13 was followed starting with 6 mmoles of 97% optically pure (−)-Tri-MCHD and using 6 mmoles of the other reagents. The product was optically active 1-phenyl-2-heptyne-1-ol. It was characterized by IR, $^1$H-NMR, mass spectral (parent ion MW=188) and elemental analysis: theory for C$_{12}$H$_{16}$O C, 82.93%; H, 8.57%. Found C, 83.75%; H, 8.54%. The product displayed $[\alpha]_{589}^{25°} -1.56°$, $[\alpha]_{589}^{25°} -3.53°$ (C, 14.3, benzene) using a Perkin-Elmer Model 141 polarimeter.

EXAMPLE 15

Following the procedure of Example 13, 1.11 g (7.1 mmoles) of (−)-Tri-MCHD was reacted with 14.9 mmoles of n-C$_4$H$_9$ Li in hexane to prepare the complex (=)-lithio-Tri-MCHD.LiC$_4$H$_9$, i.e., to prepare [Chel*-N]$^\ominus$M+M'R wherein M and M' are both lithium and R is n-butyl. The clear reaction mixture was cooled to −80° C. and 0.75 g (7.1 mmoles) of benzaldehyde was added and the reaction was treated as detailed in Example 13. Work-up afforded 0.74 g of product which by VPC analysis was 95.4% 1-phenyl-1-pentanol and 4.4% benzaldehdye. No Tri-MCHD was detected in the product. The product displayed $[\alpha]_{589}^{25°} +2.62°$ (C, 13.0, benzene) which corresponds to an optical purity of 8.4%. The product of this Example, R-(+)-1-phenyl-1-pentanol has the opposite absolute configuration to that which is obtained under identical reaction conditions when (−)-N,N,N',N'-tetramethylcyclohexanediamine.-LiC$_4$H$_9$ is added to benzaldehyde.

EXAMPLE 16

To 1.11 g (7.1 mmoles) of (−)-Tri-MCHD in 22 ml of hexane was added with stirring 3.24 g of solid obtained by stripping the solvent from commercial benzyl sodium. This formed [Chel*N]$^\ominus$M$^\oplus$M'R in which M and M' are both sodium and R is phenyl. After 20 minutes the reaction mixture was cooled to −80° C. and 0.41 g (7.1 mmoles) of propionaldehyde was added over five minutes and the reaction was subsequently treated as detailed in Example 12. Work-up afforded 0.25 g of product after vacuum stripping at 50° C. which analyzed 59.5% C$_6$H$_5$CH$_2$CH(OH)CH$_2$CH$_3$, 10% light ends and 30.5% higher boiling material. The crude product displayed $[\alpha]_{589}^{25°} +0.23°$ (C, 11.0, benzene).

EXAMPLE 17

7.1 mmoles of (−)-lithio-Tri-MCHD.LiC$_4$H$_9$ was prepared in 22 ml of hexane as described in Example 15, the mixture was cooled to −40° C., 1.35 g (7.1 mmoles) of CuI was added and after 20 minutes the reaction mixture was cooled to −80° C. Benzaldehyde, 0.75 g (7.1 mmoles), was added and the reaction was subsequently treated as described in Example 13. Work-up afforded 0.73 g of 96.5% pure 1-phenyl-1-pentanol by VPC analysis which displayed $[\alpha]_{589}^{25°} +2.99°$ (C, 13.0, benzene) which corresponds to an optical purity of 9.6%.

EXAMPLE 18

7.1 mmoles of (−)-lithio-Tri-MCHD was prepared in 22 ml of hexane as described in Example 15 and to it was added 7.1 mmoles of LiBH$_4$. The reaction mixture was cooled to −80° C. and 7 mmoles of acetophenone was added. After 30 minutes the reaction mixture was allowed to warm to room temperature and was worked-up as described in Example 13. The product was 45% pure α-phenethyl alcohol which displayed $[\alpha]_{589}^{25°} -3.42°$ (C, 13, benzene) which corresponds to 7.4% optical purity. This Example demonstrates that [Chel*]$^\ominus$M$^\oplus$M'H$_m$R$_n$X$_p$ wherein M=Li, M'=B, M=4 and n and p=0 may be used in an asymmetric synthesis process.

EXAMPLE 19

The procedure of Example 18 was followed except that that LiAlH$_4$ was substituted for LiBH$_4$ and optically active α-phenethyl alcohol having $[\alpha]_{589}^{25°} -2.26°$ (C, 13, benzene) was obtained corresponding to 4.9% optical purity.

What is claimed is:

1. Chelating tertiary amino metal amides selected from the group consisting of Mg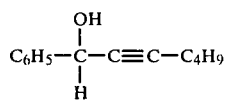 [Chel N]$_2^\ominus$ wherein [Chel N]$^\ominus$ is not

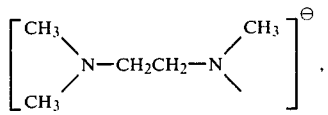

[Chel N]⊖M⊕, [Chel N]⊖M⊕M'H$_m$R$_n$X$_p$, ZMg⊕[Chel N-M'H$_m$R$_n$X$_p$]⊖, Mg(++)[Chel N M'H$_m$R$_n$X$_p$]⊖[M'H$_m$R$_n$X$_p$Z]⊕, Chel N-Mg⊖[M'H$_m$R$_n$X$_p$Z]⊖, and Mg(++)[Chel N-M'H$_m$R$_n$X$_p$]$_2$⊖, wherein M is a Group IA metal selected from the group consisting of lithium, sodium, magnesium, beryllium, zinc, cadmium, boron, aluminum, gallium, indium, zirconium, titanium, tin and copper, and m and n equal 0 to 4, p equals 0 to 3 and (m+n+p) equals the valence of M' and (m+n) equals at least 1 and X is a nonreactive group selected from the group consisting of chlorine, bromine, iodine, $C_1$-$C_{20}$ alkoxide, $C_1$-$C_{20}$ thioalkoxide, $C_2$-$C_{40}$ hydrocarbyl secondary amide and $C_2$ to $C_{40}$ hydrocarbyl secondary phosphide, R is a hydrocarbyl group selected from the group consisting of $C_1$-$C_{30}$ alkyl, $C_6$-$C_{30}$ aryl, $C_7$-$C_{30}$ aralkyl, $C_3$ to $C_{30}$ naphthenic, $C_2$ to $C_{30}$ alkenyl, $C_2$-$C_{30}$ alkynyl and cyclopentadienyl; Z is selected from the group consisting of R, X or H and [Chel N]⊕ is selected from the group consisting of compounds of the formula

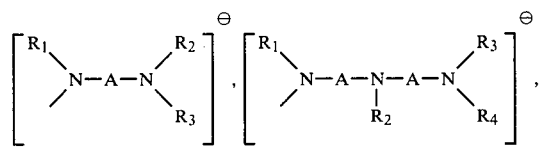

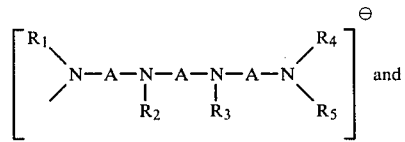

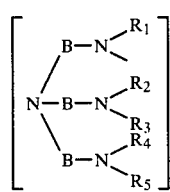

wherein $R_1$ is a $C_1$ to $C_{20}$ hydrocarbyl radical, $R_2$, $R_3$, $R_4$ and $R_5$ are the same or different alkyl or aryl radicals of 1 to 7 carbon atoms inclusive, A is selected from the group consisting of a nonreactive group containing 2 to 3 methylenic radicals having 0 to 6 monovalent substituents containing 1 to 10 carbon atoms or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 0 to 3 monovalent substituents containing 1 to 10 carbon atoms.

2. Chelating tertiary amino metal amides selected from the group consisting of [Chel N]⊖M⊕ and [Chel N]⊖M⊕-M'H$_m$R$_n$X$_p$ wherein M is a Group IA metal, M' is a metal selected from the group consisting of lithium, sodium, magnesium, beryllium, zinc, cadmium, boron, aluminum, gallium, indium, zirconium, titanium, tin and copper, and m and n equal 0 to 4, p equals 0 to 3 and (m+n+p) equals the valence of M' and (m+n) equals at least 1 and X is a nonreactive group selected from the group consisting of chlorine, bromine, iodine, $C_1$-$C_{20}$ alkoxide, $C_1$-$C_{20}$ thioalkoxide, $C_2$-$C_{40}$ hydrocarbyl secondary amide and $C_2$ to $C_{40}$ hydrocarbyl secondary phosphide, R is a hydrocarbyl group selected from the group consisting of $C_1$-$C_{30}$ alkyl, $C_6$-$C_{30}$ aryl, $C_7$-$C_{30}$ aralkyl, $C_3$ to $C_{30}$ naphthenic, $C_2$ to $C_{30}$ alkenyl, $C_2$-$C_{30}$ alkynyl and cyclopentadienyl; Z is selected from the group consisting of R, X or H and [Chel N]⊖ is selected from the group consisting of compounds of the formulae:

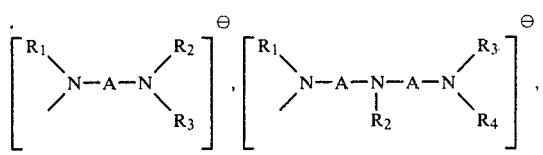

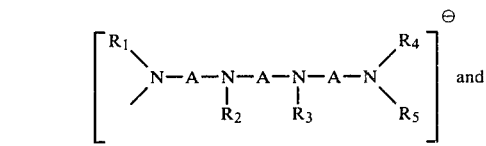

wherein $R_1$ is a $C_1$ to $C_{20}$ hydrocarbyl radical, $R_2$, $R_3$, $R_4$ and $R_5$ are the same or different alkyl or aryl radicals of 1 to 7 cirbon atoms inclusive, A is selected from the group consisting of a nonreactive group containing 2 to 3 methylenic radicals having 0 to 6 monovalent substituents containing 1 to 10 carbon atoms or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 0 to 3 monovalent substituents containing 1 to 10 carbon atoms.

3. Optically active chelating tertiary amino metal amides selected from the group consisting of [Chel*-N]⊖M⊕, [Chel*N]⊖M⊕M'H$_m$R$_n$X$_p$, ZMg⊕[Chel*-N-M'H$_m$R$_n$X$_p$]⊖, Mg(++)-[Chel*N M'H$_m$R$_n$X$_p$]⊖[M'H$_m$R$_n$X$_p$Z]⊖, Chel*-N-Mg⊕[M'H$_m$R$_n$X$_p$Z]⊖, Mg(++)[Chel*-N-M'H$_m$R$_n$X$_p$]$_2$⊖ and Mg(++)[Chel*N]$_2$⊖ wherein [Chel*N]⊖ has a formula selected from the group consisting of

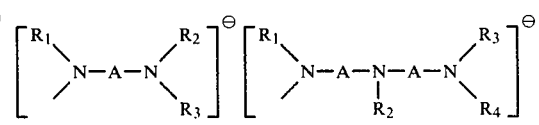

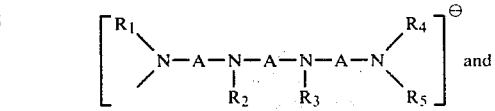

-continued

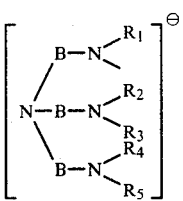

wherein R₁ is a $C_1$ to $C_{20}$ hydrocarbyl radical; R₂, R₃, R₄ and R₅ are the same or different alkyl or aryl radicals of 1 to 7 carbon atoms inclusive; A is selected from the group consisting of a nonreactive group containing 2 to 3 methylenic radicals having 1 to 6 monovalent substituents containing 1 to 10 carbon atoms or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 1 to 3 monovalent substituents containing 1 to 10 carbon atoms such that the chelating tertiary amino amide does not have a center, plane or alternating axis of symmetry; M is a Group IA metal, M' is a metal selected from the group consisting of lithium, sodium, beryllium, magnesium, zinc, copper, cadmium, boron, aluminum, gallium, indium, zirconium, titanium, and tin and m and n equal 0 to 4, p equals 0 to 3, (m+n+p) equals the valence of M' and (m+n) equals at least 1; R is a hydrocarbyl group selected from the group consisting of $C_1$-$C_{30}$ alkyl, $C_6$-$C_{30}$ aryl, $C_7$-$C_{30}$ aralkyl, $C_3$-$C_{30}$ naphthenic, $C_2$-$C_{30}$ alkenyl, $C_2$-$C_{30}$ alkynyl and cyclopentadienyl, X is a nonreactive group selected from the group consisting of chlorine, bromine, iodine, $C_1$-$C_{20}$ alkoxide, $C_1$-$C_{20}$ thioalkoxide, $C_2$-$C_{40}$ hydrocarbyl secondary amide and $C_2$-$C_{40}$ hydrocarbyl secondary phosphide, Z is selected from the group consisting of R, X or H as previously defined and * denotes optical activity.

4. Optically active chelating tertiary amino metal amides according to claim 3 wherein R₁ is a $C_1$ to $C_{20}$ hydrocarbyl radical; R₂, R₃, R₄ and R₅ are the same or different alkyl radicals of 1 to 4 carbon atoms inclusive; A is selected from the group consisting of a nonreactive group containing 2 to 3 methylenic radicals having 1 to 3 monovalent substituents containing 1 to 10 carbon atoms or a cyclohexyl radical and its lower alkyl or naphthenic derivatives wherein said radical is attached to the nitrogen atoms in a trans fashion at adjacent positions on the ring such that the chelating tertiary amino metal amide does not have a center, plane or alternating axis of symmetry.

5. Optically active diamine and triamine chelating tertiary amino metal amides according to claim 3 wherein R₁ is a $C_1$ to $C_{20}$ hydrocarbyl radical; R₂, R₃, R₄ and R₅ are methyl groups; A is selected from the group consisting of a nonreactive group containing 2 methylenic radicals having 1 to 2 monovalent substituents containing 1 to 6 carbon atoms or a cyclohexyl radical and its lower alkyl or naphthenic derivatives, wherein said radical is attached to the nitrogen atoms in a trans fashion, at adjacent positions on the ring such that the chelating tertiary amino metal amide does not have a center, plane or alternating axis of symmetry.

6. Optically active chelating tertiary amino metal amides selected from the group consisting of [Chel*-N]⊖M⊕, [Chel*N]₂⊖Mg⊕⊕, [Chel*-N]⊖M⊕M'H$_m$R$_n$X$_p$, ZMg⊕[Chel*N]⊕M'H$_m$R$_n$X$_p$, Mg⊕⊕([Chel*N]M'H$_m$R$_n$X$_p$)⊖-(M'H$_m$R$_n$X$_p$Z)⊖, Chel*N-Mg+[M'H$_m$R$_n$X$_p$Z]⊖ and Mg⊕⊕ -[Chel*-N-M'H$_m$R$_n$X$_p$]₂⊖ wherein [Chel*N]⊖ has a formula selected from the group consisting of

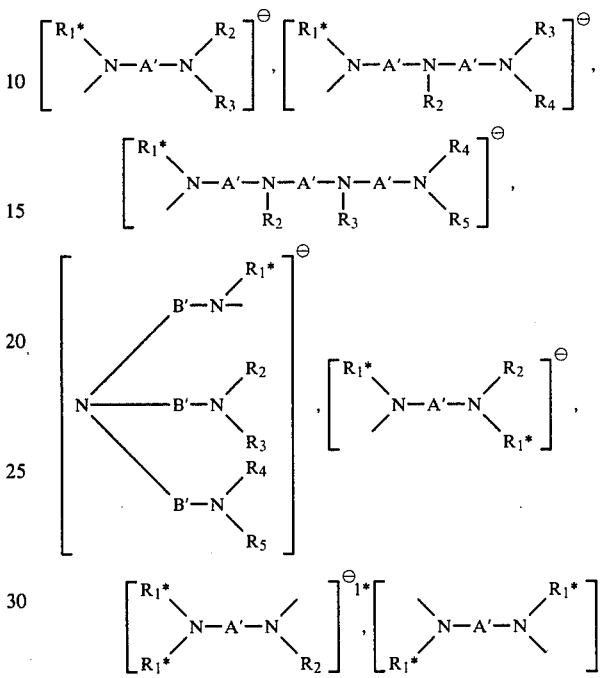

wherein R₁* is a $C_4$ to $C_{20}$ hydrocarbyl group containing at least one resolved asymmetric carbon atom which is removed no more than 4 carbon atoms from the nitrogen atoms; A' is a nonreactive group containing 2 to 3 methylene radicals or a cycloaliphatic radical and their lower alkyl or naphthenic derivatives having ring structures containing 5 to 7 members wherein said radicals are attached to the nitrogen atoms at adjacent positions on the rings; B' is a nonreactive group containing 2 to 3 methylenic radicals; R₂-R₅, M, M', R, X, m, n and p are as defined in claim 3.

7. Optically active chelating tertiary amino metal amides according to claim 3 wherein [Chel*N]⊖ is

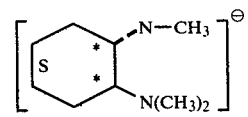

8. Optically active chelating tertiary amino metal amides according to claim 3 wherein [Chel*N]⊖ is

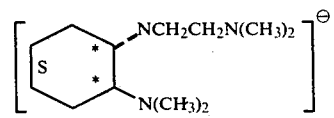

9. Optically active chelating tertiary amino metal amides according to claim 3 wherein [Chel*N]⊖ is

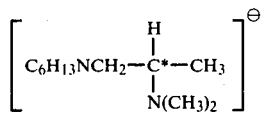

10. Optically active chelating tertiary amino metal amides according to claim 3 wherein [Chel*N]⁻ is

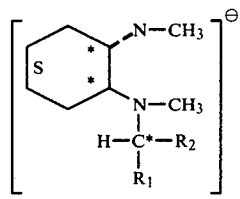

wherein R₁ and R₂ are as defined in claim 3.

11. Optically active chelating tertiary amino metal amide according to claim 3 of the formula:

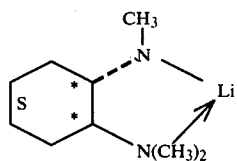

12. Optically active chelating tertiary amino metal amide according to claim 3 of the formula:

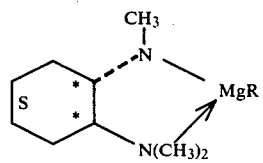

wherein R is selected from the group consisting of secondary butyl and phenyl.

13. Optically active chelating tertiary amino metal amide according to claim 3 of the formula:

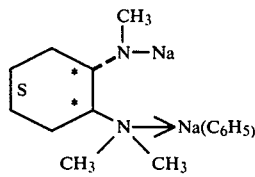

14. Optically active chelating tertiary amino metal amide according to claim 3 of the formula:

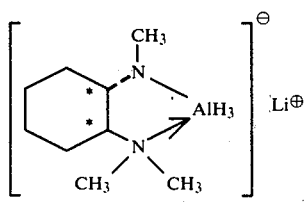

15. Optically active chelating tertiary amino metal amide according to claim 3 of the formula:

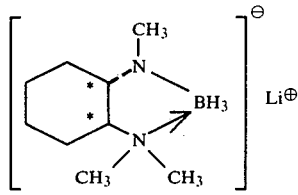

16. An asymmetric synthesis process for preparing optically active compounds which comprises the step of reacting an (a) organometal compound selected from the metal group of lithium, sodium, beryllium, magnesium, zinc, copper, cadmium, zirconium, gallium, titanium complexed to an optically active chelating tertiary amino metal amide having an amide formula [Chel*-N]⁻ selected from the group consisting of those compounds defined in claimed 4; with (b) a prochiral unsaturated compound.

17. A process according to claim 16 wherein the prochiral unsaturated compounds are selected from the group consisting of aldehydes, ketones, amines, oximes and hydrozones.

18. A process according to claim 16 in which the organometal compound is an organolithium compound.

19. A process according to claim 16 in which the organometal compound is an organosodium compound.

20. A process according to claim 16 in which the organometal compound is an organomagnesium compound.

21. Chelating tertiary amino metal amides selected from the group consisting of:

$$[Chel\ N]^\ominus M^\oplus M'H_m R_n X_p$$

wherein M is a group IA metal, M' is a metal selected from the group consisting of aluminum, gallium, boron and indium, m and n equal 0 to 4, p equals 0 to 3 and (m+n+p) equals the valence of M' and (m+n) equals at least 1 and X is a nonreactive group selected from the group consisting of chlorine, bromine, iodine, C₁–C₂₀ alkoxide, C₁–C₂₀ thioalkoxide, C₂–C₄₀ hydrocarbyl secondary amide and C₂–C₄₀ hydrocarbyl secondary phosphide, R is a hydrocarbyl group selected from the group consisting of C₁–C₃₀ alkyl, C₆–C₃₀ aryl, C₇–C₃₀ aralkyl, C₃–C₃₀ naphthenic, C₂–C₃₀ alkenyl, C₂–C₃₀ alkynyl and cyclopentadienyl and wherein [Chel N]⁻ has the formula:

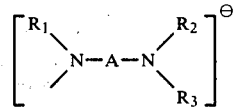

wherein R₁ is a C₁–C₂₀ hydrocarbyl radical; R₂ and R₃ are the same or different alkyl or aryl radicals of 1 to 7 carbon atoms inclusive; A is selected from the group consisting of a nonreactive group containing 2 to 3 methylenic radicals having 0 to 6 monovalent substituents containing 1 to 10 carbon atoms or is a cycloaliphatic radical and their lower alkyl or naphthenic derivatives having ring structures containing 5 to 7 members wherein said radicals are attached to the nitrogen atoms at adjacent positions on the rings.

* * * * *